US012779240B2

(12) United States Patent
Kerber

(10) Patent No.: US 12,779,240 B2
(45) Date of Patent: Nov. 3, 2026

(54) THERAPY LIGHT WITH VENTILATED LED CIRCUIT BOARD

(71) Applicant: Thomas Kerber, Hamilton (CA)

(72) Inventor: Thomas Kerber, Hamilton (CA)

( * ) Notice: Subject to any disclaimer, the term of this patent is extended or adjusted under 35 U.S.C. 154(b) by 53 days.

(21) Appl. No.: 18/097,987

(22) Filed: Jan. 17, 2023

(65) Prior Publication Data

US 2026/0007900 A1 Jan. 8, 2026

(51) Int. Cl.
*A61N 5/06* (2006.01)

(52) U.S. Cl.
CPC ........ *A61N 5/06* (2013.01); *A61N 2005/0632* (2013.01); *A61N 2005/0652* (2013.01)

(58) Field of Classification Search
None
See application file for complete search history.

(56) References Cited

U.S. PATENT DOCUMENTS 8,123,381 B1 * 2/2012 Wray ........................ F21K 9/23 362/373
2003/0076033 A1 * 4/2003 Wu ........................... G09F 9/33 257/E25.02
2004/0232359 A1 * 11/2004 Fiset .................... A61N 5/0614 250/504 R
2006/0064144 A1 * 3/2006 Chen .................... A61N 5/0618 607/90
2007/0279930 A1 * 12/2007 Aoki ................. G02F 1/133608 362/561
2018/0352650 A1 * 12/2018 Dijken ................... H05K 3/445
2022/0416205 A1 * 12/2022 Pang .................... H10K 50/844

OTHER PUBLICATIONS

Cree Inc., CreeÂ® XLampÂ® XR-E LED, Product Family Data Sheet, 2006-2015. (Year: 2015).*

* cited by examiner

*Primary Examiner* — Manolis Pahakis

(57) ABSTRACT

A therapy light comprises a housing and a circuit board mounted within the housing and having light emitting diodes mounted thereon. Airflow apertures in the circuit board are disposed adjacent the light emitting diodes such that the front face and the back face of the circuit board are in airflow communication one with the other. The ratio of the cumulative cross-sectional area of the airflow apertures to the cumulative cross-sectional area of the light emitting diodes is greater than about 3:2. In use, a fan causes air to flow into an intake ventilation opening, from the intake ventilation opening to the circuit board, through the airflow apertures in the circuit board, and out of an exhaust ventilation opening, to thereby cool the light emitting diodes.

13 Claims, 5 Drawing Sheets

THERAPY LIGHT WITH VENTILATED LED CIRCUIT BOARD

FIELD OF THE INVENTION

The present invention relates to therapy lights, and more particularly to therapy lights having one or more ventilated LED circuit boards.

BACKGROUND OF THE INVENTION

It has been found that in many applications, such as medical healing applications, light can be effective in generally helping the human body to heal itself, and also can be effective in providing energy as a catalyst for various pharmaceutical drugs used in treatment of the human body. While various therapy lights are available, there is a great need for therapy lights that produce intense light output in order to penetrate live tissue in order to provide healing, and also to remain below a temperature that would be uncomfortable or even injurious to a person or animal.

The relevant known prior art therapy lights will now be discussed.

U.S. Pat. No. 5,121,290, issued Jun. 9, 1992 to Azar and entitled Circuit Pack Cooling Using Perforations, discloses an apparatus for providing forced air cooling of components mounted on circuit boards in a stacked configuration. A plurality of perforations is provided in the circuit boards so that air flow in the channel between boards causes air to be sucked through the perforations to eliminate stagnant areas between components and provide local jet impingement cooling.

U.S. Pat. No. 7,218,517, issued May 15, 2007 to Wolford et al and entitled Cooling Apparatus For Vertically Stacked Printed Circuit Boards, discloses an apparatus, system and method for cooling vertically stacked printed circuit boards (PCBs). In one embodiment, a first PCB is disposed within a substantially enclosed lower chamber inside a PCB containment housing. A second PCB is disposed above the first PCB within the housing to define a substantially enclosed upper chamber above the lower chamber. The second PCB includes one or more airflow apertures defined therethrough and providing vertical air flow coupling between the upper and lower chambers. An airflow actuating device is utilized to generate a primary forced airflow within the upper chamber which is substantially parallel to the surface plane of the second PCB. The primary forced airflow further induces a negative air pressure in the upper chamber such that a mixed convection airflow is established between the upper and lower chambers via the second PCB apertures.

United States Published Patent Application No. 2006/0104025, published May 18, 2006 to Wabiszczewicz and entitled PCB With Forced Airflow And Device Provided With PCB With Forced Airflow, discloses a device with a PCB with forced airflow has a housing including a first panel and a second panel. Within the housing is mounted a printed circuit board with heat dissipating elements, an opening, a first surface and a second surface. The first surface of the printed circuit board is located at a distance from the first panel smaller than a distance between the second surface and the second panel. To the printed circuit board is mounted a fan that covers the opening and forces airflow from a space between the first surface and the first panel to a space adjacent the second surface.

U.S. Pat. No. 6,924,447, issued Aug. 2, 2005 to Lu et al and entitled Waterproof Structure of Printed Circuit Board, discloses a waterproof structure used with a printed circuit board, which is primarily composed of an upper layer membrane, a lower layer membrane, and an insulation layer, which are conjoined to one another. Besides, at least one first channel and second channel are provided on the upper layer membrane and the lower layer membrane respectively and correspondingly. Also, a pressure-adjusting hole, whose periphery is larger than that of the first channel and the second channel, is provided on the insulation layer corresponding to the positions of the first channel and the second channel. After the first channel, the second channel, and the pressure-adjusting hole of the insulation layer have been conjoined, a waterproof unit will be formed at a place where the contact points of the three are not connected to one another. The waterproof unit contains circulated air and prevents moisture from permeating into the circuit board thereby avoiding a short circuit of the circuit board.

U.S. Pat. No. RE 44,628 E, re-issued Dec. 10, 2013 to Ramalingam et al and entitled Process for Assembling an Integrated Circuit Package Having a Substrate Vent Hole, discloses a method of providing an integrated circuit package having a substrate with a vent opening. The integrated circuit package includes the substrate having an opening and an integrated circuit mounted to the substrate. An underfill material is dispensed between the substrate and the integrated circuit.

U.S. Pat. No. 9,818,703, issued Nov. 14, 2017 to Jang et al and entitled Printed Circuit Board, discloses a printed circuit board that includes chip regions on which semiconductor chips are mounted, and a scribe region surrounding each of the chip regions. The scribe region includes first vent holes that are configured to receive a flow of molding resin and are arranged along a first direction corresponding to a flow direction of the molding resin.

It is an object of the present invention to provide a therapy light.

It is an object of the present invention to provide a therapy light that is properly ventilated.

It is an object of the present invention to provide a therapy light that produces intense light output.

It is an object of the present invention to provide a therapy light that produces intense light output having an irradiance intensity of greater than 80 $mW/cm^2$.

It is an object of the present invention to provide a therapy light that produces intense light output in order to penetrate live tissue to thereby provide healing.

It is an object of the present invention to provide a therapy light that produces intense light output and remains below a temperature that would be uncomfortable or even injurious to a person or animal.

It is an object of the present invention to provide a therapy light that is lightweight.

It is an object of the present invention to provide a therapy light that is readily manufacturable.

It is an object of the present invention to provide a therapy light that is inexpensive to manufacture.

It is another object of the present invention to provide a therapy light that is convenient to use.

It is a further object of the present invention to provide a therapy light that is safe to use.

It is an object of the present invention to provide a ventilated LED circuit board for use in a therapy light.

It is an object of the present invention to provide a ventilated LED circuit board for use in a therapy light, wherein the LED circuit board is properly ventilated.

It is an object of the present invention to provide a ventilated LED circuit board for use in a therapy light that produces intense light output.

It is an object of the present invention to provide a ventilated LED circuit board for use in a therapy light that produces intense light output having an irradiance intensity of greater than 80 $mW/cm^2$.

It is an object of the present invention to provide a ventilated LED circuit board for use in a therapy light, wherein the LED circuit board produces intense light output in order to penetrate live tissue to thereby provide healing.

It is an object of the present invention to provide a ventilated LED circuit board for use in a therapy light, wherein the LED circuit board produces intense light output and the therapy light remains below a temperature that would be uncomfortable or even injurious to a person or animal.

It is an object of the present invention to provide a ventilated LED circuit board for use in a therapy light, wherein the LED circuit board and the therapy light are lightweight.

It is an object of the present invention to provide a ventilated LED circuit board for use in a therapy light, wherein the LED circuit board and the therapy light are readily manufacturable.

It is an object of the present invention to provide a ventilated LED circuit board for use in a therapy light, wherein the LED circuit board and the therapy light are inexpensive to manufacture.

It is another object of the present invention to provide a ventilated LED circuit board for use in a therapy light, wherein the therapy light is convenient to use.

It is a further object of the present invention to provide a ventilated LED circuit board for use in a therapy light, wherein the therapy light is safe to use.

SUMMARY OF THE INVENTION

In accordance with one aspect of the present invention there is disclosed a novel therapy light comprising a housing having a main opening for emitting light therefrom and defining an interior chamber. A circuit board has a front face and a back face and is operatively mounted within the interior chamber of the housing. A plurality of light emitting diodes are operatively mounted on the front face of the circuit board so as to face the main opening, for emitting light through the main opening. An intake ventilation opening in the housing permits the ingress of airflow into the interior chamber of the housing. An exhaust ventilation opening in the housing permits the egress of airflow heated by the light emitting diodes from the housing. A plurality of airflow apertures in the circuit board are disposed adjacent the light emitting diodes such that the front face and the back face of the circuit board are in airflow communication one with the other and the intake ventilation opening and the exhaust ventilation opening are interconnected in airflow communication one with the other. The ratio of the cumulative cross-sectional area of the airflow apertures to the cumulative cross-sectional area of the light emitting diodes is greater than about 3:2. An airflow generating apparatus has an air inlet disposed in air-receiving relation with respect to the intake ventilation opening and an air outlet disposed in air-delivering relation with respect to the exhaust ventilation opening. In use, the airflow generating apparatus causes air to flow into the intake ventilation opening, from the intake ventilation opening to one of the front face and the back face of the circuit board, through the plurality of airflow apertures to the other one of the front face and the back face of the circuit board, and out of the exhaust ventilation opening, to thereby cool the light emitting diodes.

In accordance with another aspect of the present invention there is disclosed a novel circuit board assembly comprising a circuit board having a front face and a back face. A plurality of light emitting diodes are operatively mounted on the front face of the circuit board. A plurality of airflow apertures in the circuit board are disposed adjacent the light emitting diodes such that the front face and the back face of the circuit board are in airflow communication one with the other. The ratio of the cumulative cross-sectional area of the airflow apertures to the cumulative cross-sectional area of the light emitting diodes is greater than about 3:2.

Other advantages, features and characteristics of the present invention, as well as methods of operation and functions of the related elements of the structure, and the combination of parts and economies of manufacture, will become more apparent upon consideration of the following detailed description and the appended claims with reference to the accompanying drawings, the latter of which is briefly described herein below.

BRIEF DESCRIPTION OF THE DRAWINGS

The novel features which are believed to be characteristic of the therapy light with vented circuit board according to the present invention, as to its structure, organization, use and method of operation, together with further objectives and advantages thereof, will be better understood from the following drawings in which a presently described embodiment of the invention will now be illustrated by way of example. It is expressly understood, however, that the drawings are for the purpose of illustration and description only, and are not intended as a definition of the limits of the invention. In the accompanying drawings.

COMPONENT LIST

Figure 1:
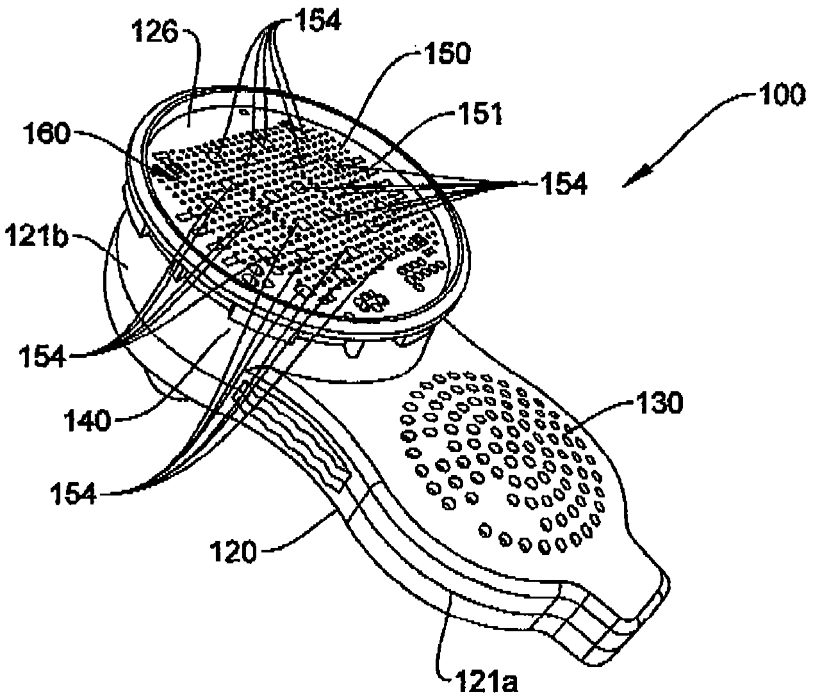
FIG. 1 is a perspective view from the side of the illustrated embodiment of the therapy light having a ventilated LED circuit board according to the present invention.
Figure 2:
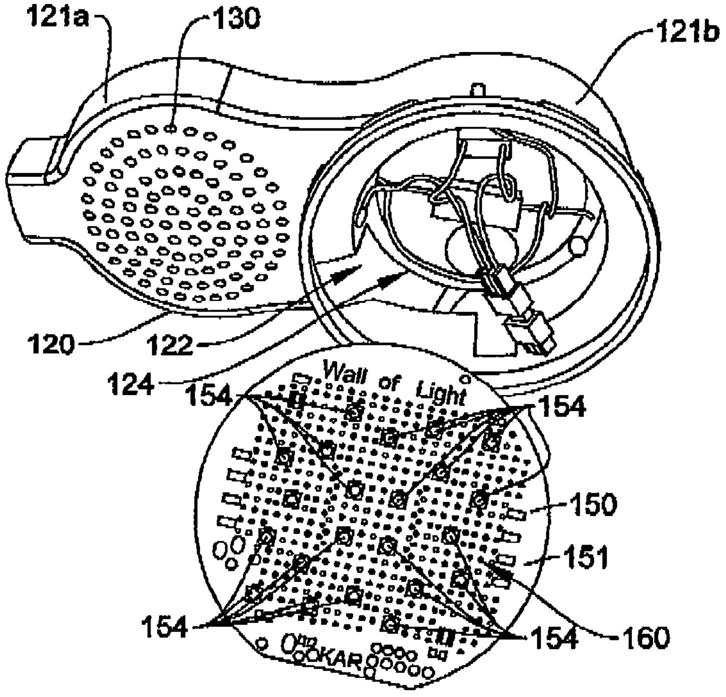
FIG. 2 is a perspective view from the front of the illustrated embodiment of the therapy light having a ventilated LED circuit board of FIG. 1, with the circuit board removed from the housing for the sake of illustration.
Figure 4:
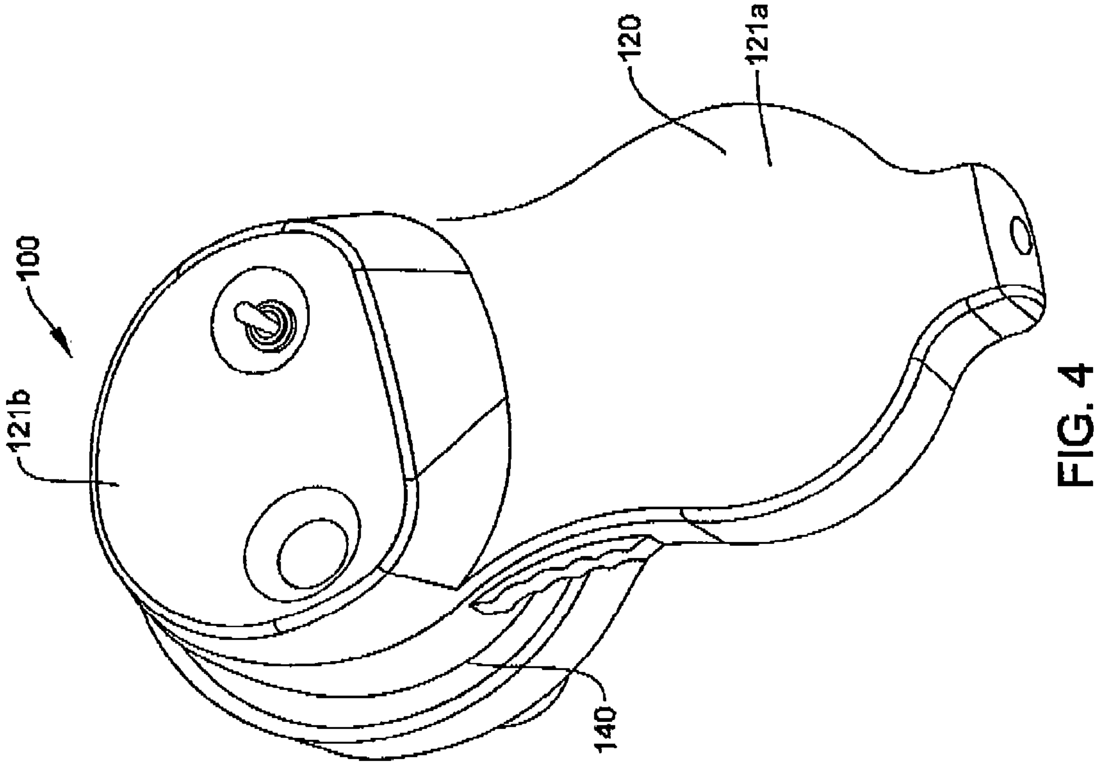
FIG. 4 is a rear elevational view of the illustrated embodiment of the therapy light having a ventilated LED circuit board of FIG. 1.
Figure 3:
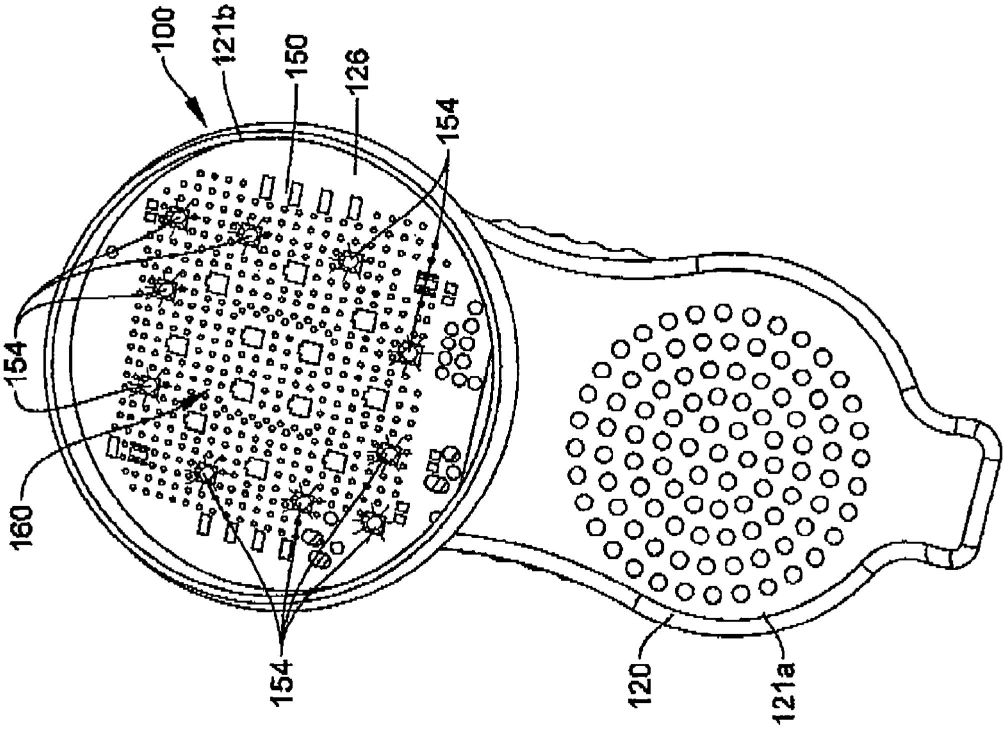
FIG. 3 is a front elevational view of the illustrated embodiment of the therapy light having a ventilated LED circuit board of FIG. 1.
Figure 6:
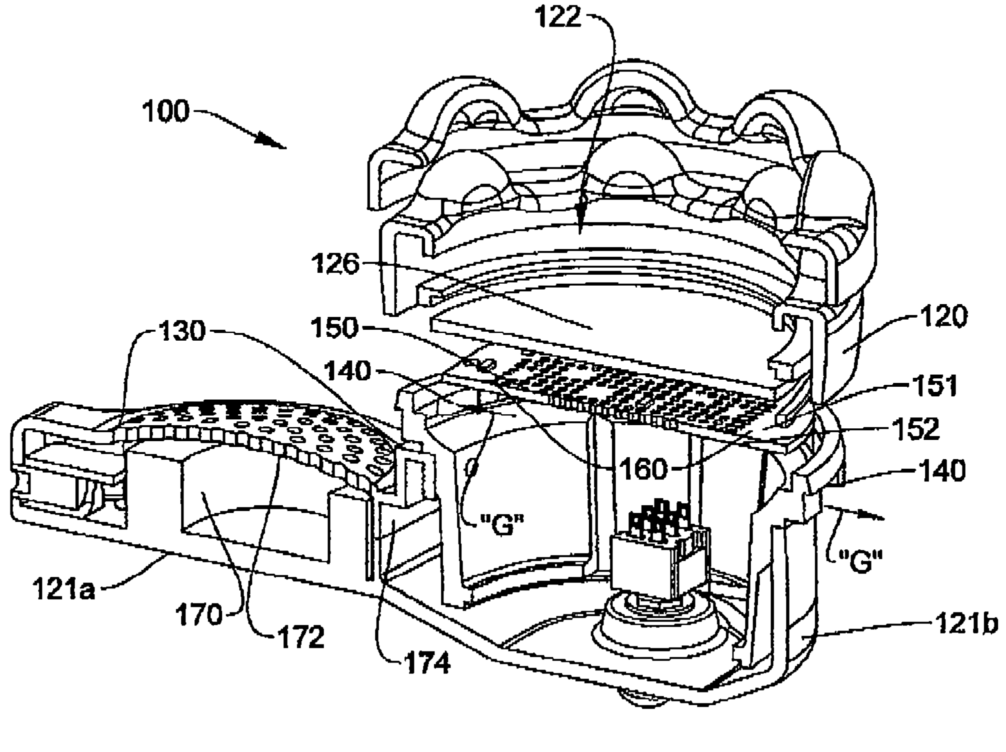
FIG. 6 is a perspective cross-sectional side elevational view of the illustrated embodiment of the therapy light with ventilated LED circuit board of FIG. 1, taken along section line 5-5 of FIG. 3, and showing the flow path of air through the therapy light.

100 therapy light
120 housing
121*a* handle portion
121*b* head portion
122 main opening
124 interior chamber
126 transparent lens
130 intake ventilation opening
140 exhaust ventilation opening
150 ventilated LED circuit board
151 front face
152 back face
154 plurality of light emitting diodes
160 airflow apertures
170 airflow generating apparatus
172 air inlet
174 air outlet

DETAILED DESCRIPTION OF THE ILLUSTRATED EMBODIMENT

Reference will now be made to FIGS. 1 through 8, which show an illustrated embodiment of the therapy light according to the present invention, as indicated by general reference numeral 100. The therapy light 100 may be used, for instance, in providing treatment for a person or an animal.

In brief, the therapy light 100 comprises a housing 120, a ventilated LED circuit board 150, and an airflow generating apparatus 170.

More specifically, the housing 120 has a handle portion 121*a* and a head portion 121*b*, with the ventilated LED circuit board 150 mounted in the head portion 120*b*. There is a main opening 122 in the head portion 120*b* for emitting light therefrom. The handle portion 121*a* and the head portion 121*b* together define an interior chamber 124. There is transparent lens 126 made from a suitable plastic or glass material, or the like. The transparent lens 126 precludes direct contact by a person or animal with the LED circuit board 150.

There is an intake ventilation opening 130 in the housing 120 for permitting the ingress of airflow into the interior chamber 124 of the housing 120. As illustrated, the intake ventilation opening 130 comprises a large plurality of adjacent intake ventilation openings 130 in the handle portion 121*a* of the housing 120.

There is also an exhaust ventilation opening 140 in the housing 120 for permitting the egress of airflow heated by the light emitting diodes 154 from the housing 120. As illustrated, the exhaust ventilation opening 140 the comprises a plurality of exhaust ventilation openings 140 in the head portion 121*b* of the housing 120.

The intake ventilation opening 130 and the exhaust ventilation opening 140 are in fluid communication each with the other through the interior chamber 124 of the housing 120.

The LED circuit board 150 has a front face 151 and a back face 152 and is operatively mounted within the interior chamber 124 of the housing 120. A plurality of light emitting diodes 154 are operatively mounted on the front face 151 of the ventilated LED circuit board 150 so as to face the main opening 122, for emitting light through the main opening 122. It has been found that aluminum-core printed circuit boards work well for conducting heat from the front face 151 to the back face 152.

A plurality of airflow apertures 160 are formed in the ventilated LED circuit board 150, disposed adjacent the light emitting diodes 154 such that the front face 151 and the back face 152 of the ventilated LED circuit board 150 are in airflow communication one with the other and the intake ventilation opening 130 and the exhaust ventilation opening 140 are interconnected in airflow communication one with the other. The ratio of the cumulative cross-sectional area of the airflow apertures 160 to the cumulative cross-sectional area of the light emitting diodes 154 is greater than about 3:2.

In the present invention, the ratio of the cumulative cross-sectional area of the airflow apertures 160 to the cumulative cross-sectional area of the light emitting diodes 154 is greater than about 7:4. Even more specifically, the ratio of the cumulative cross-sectional area of the airflow apertures 160 to the cumulative cross-sectional area of the light emitting diodes 154 is less than about 10:4.

Also, in the present invention, the ratio of the cross-sectional area of the airflow apertures 160 to the cross-sectional area of the light emitting diodes 154 is between about 1:5 and 1:1. Even more specifically, the ratio of the cross-sectional area of the airflow apertures 160 to the cross-sectional area of the light emitting diodes 154 is less than about 1:3.

Also, in the present invention, the diameter of the airflow apertures 160 is between 0.5 millimeters and 1.5 millimeters. Even more specifically, the diameter of the airflow apertures 160 is about 1. millimeter.

Further, in the present invention, the overall density of the airflow apertures 160 in a ventilated area of the ventilated LED circuit board 150 is between ten (10) airflow apertures 160 per square centimeter and twenty (20) airflow apertures 160 per square centimeter. Even more specifically, the overall density of the airflow apertures 160 in a ventilated area of the ventilated LED circuit board 150 is about fifteen (15) airflow apertures 160 per square centimeter.

As illustrated, but not necessarily, the airflow apertures 160 are arranged generally in a grid pattern. Any other suitable pattern can be used.

The airflow generating apparatus 170 has an air inlet 172 disposed in air-receiving relation with respect to the intake ventilation opening 130 and an air outlet 174 disposed in air-delivering relation with respect to the exhaust ventilation opening 140. As illustrated, but not necessarily, the air flow generating apparatus comprises a blower fan 170.

Figure 5:
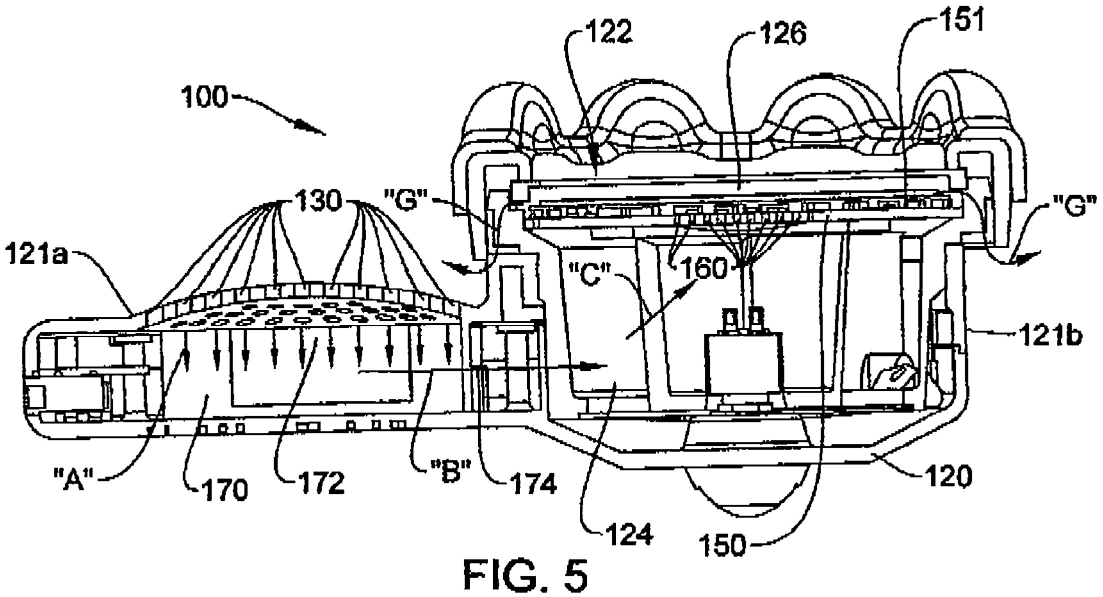
FIG. 5 is a cross-sectional side elevational view of the illustrated embodiment of the therapy light with ventilated LED circuit board of FIG. 1, taken along section line 5-5 of FIG. 3.
Figure 5A:
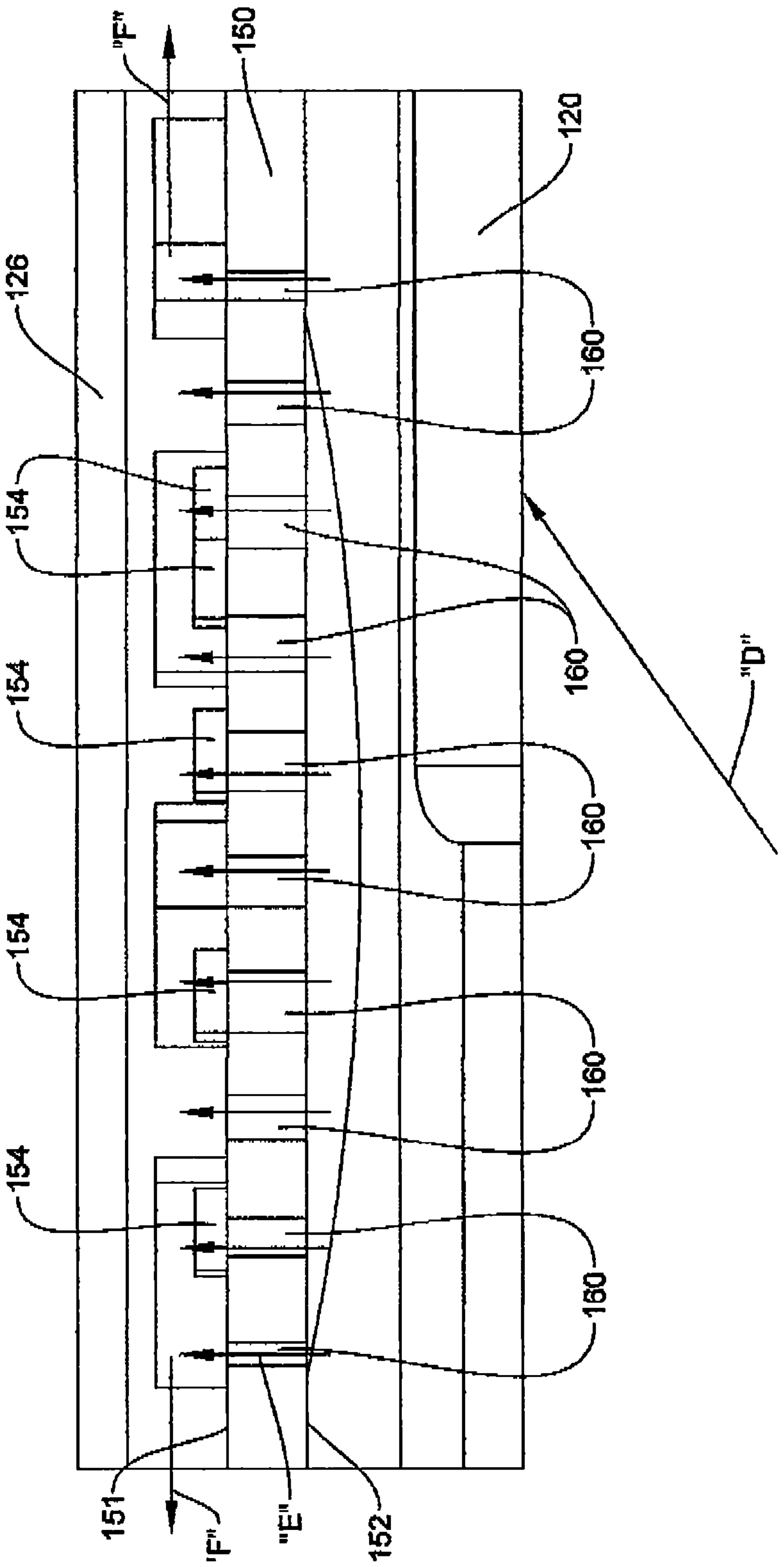
FIG. 5A is an enlarged sectional side elevational view of a portion the illustrated embodiment of the therapy light with ventilated LED circuit board of FIG. 6, to show characteristics of the ventilated LED circuit board, and showing the flow path of air through the therapy light.
Figure 7:
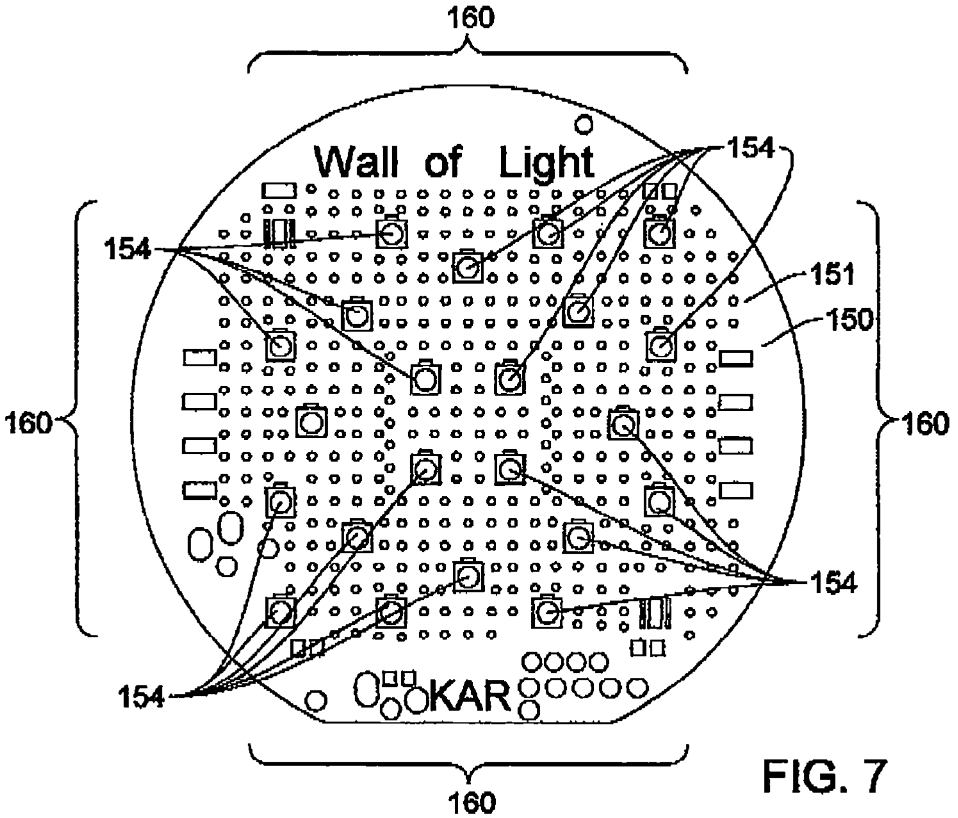
FIG. 7 is an enlarged front elevational view of the ventilated LED circuit board of FIG. 1; and, FIG. 8 is an enlarged front elevational view of the ventilated LED circuit board as shown in FIG. 7, with no components mounted on it.
Figure 8:
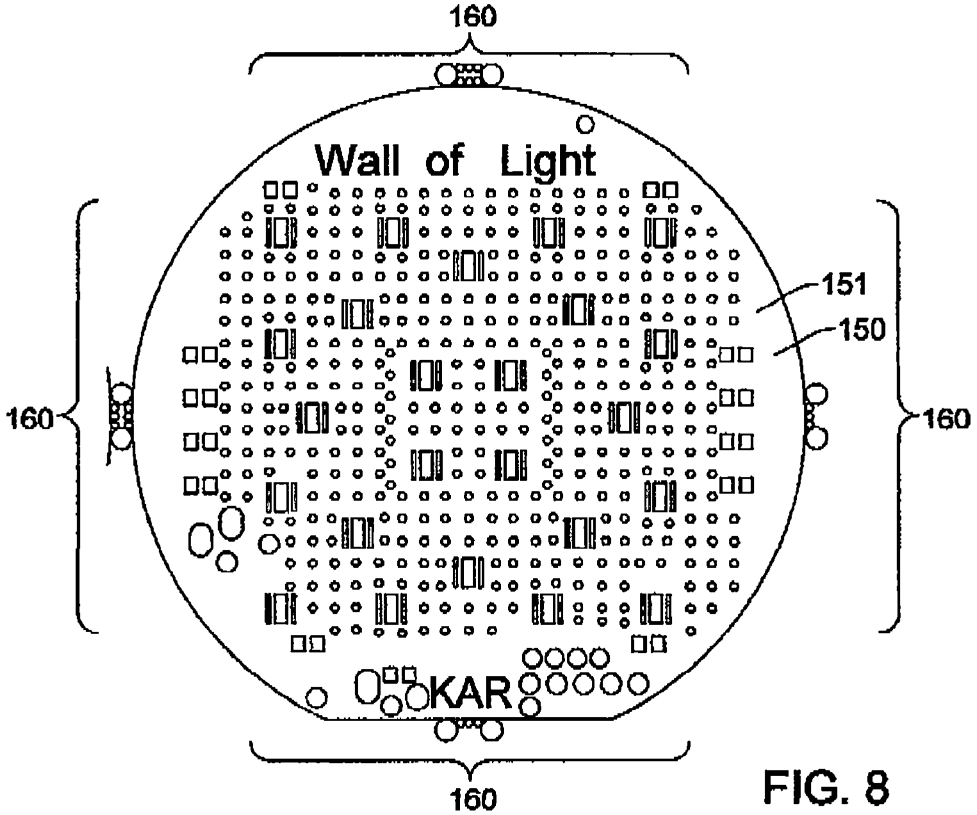

In use, the airflow generating apparatus 170 causes air to flow into and through the intake ventilation opening 130 (arrows "A" in FIGS. 5 and 6), from the intake ventilation opening 130 to one of the front face 151 and the back face 152 of the ventilated LED circuit board 150. In the illustrated embodiment, air flows from the intake ventilation opening 130 to the front face 151 of the ventilated LED circuit board 150 (arrows "B" and "C" in FIGS. 5 and 6, and arrows "D" in FIG. 5A), through the airflow apertures 160 in the ventilated LED circuit board 150 (arrows "E" in FIG. 5A) to the other one of the front face 151 and the back face 152 of the circuit board 150, which in this case is the back face 152 of the circuit board 150, to thereby immediately contact and cool the light emitting diodes 154. The airflow is then directed to the exhaust ventilation openings 140 in the head portion 121*b* of the housing 120 (arrows "F" in FIG. 5A) and then through and out of the exhaust ventilation openings 140, to thereby cool the light emitting diodes 154 and correspondingly cool the therapy light 100.

As can be understood from the above description and from the accompanying drawings, the present invention provides a therapy light that is properly ventilated, that produces intense light output, that produces intense light output having an irradiance intensity of greater than 80 $mW/cm^2$, that produces intense light output in order to penetrate live tissue to thereby provide healing, that produces intense light output and remains below a temperature that would be uncomfortable or even injurious to a person or animal, that is lightweight, that is readily manufacturable, that is inexpensive to manufacture, that is convenient to use, and that is safe to use, and provide a ventilated LED circuit board for use in a therapy light, a ventilated LED circuit board for use in a therapy light wherein the LED circuit board is properly ventilated, that produces intense light output, that produces intense light output having an irradiance intensity of greater than 80 $mW/cm^2$, wherein the LED circuit board produces intense light output in order to penetrate live tissue to thereby provide healing, wherein the LED circuit board produces intense light output and the therapy light remains below a temperature that would be uncomfortable or even injurious to a person or animal, wherein the LED circuit board and the therapy light are lightweight, wherein the LED circuit board and the therapy light are readily manufacturable, wherein the LED circuit board and the therapy light are inexpensive to manufacture, wherein the therapy light is convenient to use, and wherein the therapy light is safe to use.

Other variations of the above principles will be apparent to those who are knowledgeable in the field of the invention, and such variations are considered to be within the scope of the present invention. For instance, the light assembly could comprise something more similar to a light bulb, or alternatively could be made from flexible plastic to enable it to be placed on the arm, leg or torso of a person, for instance. Further, other modifications and alterations may be used in the design and manufacture of the light assembly of the present invention without departing from the spirit and scope of the accompanying claims.

I claim:

1. A therapy light comprising:

a housing having a main opening for emitting light therefrom and defining an interior chamber;

a circuit board having a front face and a back face and operatively mounted within said interior chamber of said housing;

a plurality of light emitting diodes operatively mounted on said front face of said circuit board so as to face said main opening, for emitting light through said main opening;

an intake ventilation opening in said housing for permitting said ingress of airflow into said interior chamber of said housing; an exhaust ventilation opening in said housing for permitting said egress of airflow heated by said light emitting diodes from said housing;

a plurality of airflow apertures in said circuit board disposed adjacent said light emitting diodes such that said front face and said back face of said circuit board are in airflow communication one with the other and said intake ventilation opening and said exhaust ventilation opening are interconnected in airflow communication one with the other, wherein the ratio of the cumulative cross-sectional area of the airflow apertures to the cumulative cross-sectional area of the light emitting diodes is greater than 3:2;

an airflow generating apparatus having an air inlet disposed in air-receiving relation with respect to said intake ventilation opening and an air outlet disposed in air-delivering relation with respect to said exhaust ventilation opening;

wherein, in use, said airflow generating apparatus causes air to flow into said intake ventilation opening, from said intake ventilation opening to one of said front face and said back face of said circuit board, through said plurality of airflow apertures to the other one of said front face and said back face of said circuit board, and out of said exhaust ventilation opening, to thereby cool said light emitting diodes; and wherein the overall density of the airflow apertures in a ventilated area of the circuit board is between ten airflow apertures per square centimeter and twenty airflow apertures per square centimeter.

2. The therapy light of claim 1, wherein the ratio of the cumulative cross-sectional area of the airflow apertures to the cumulative cross-sectional area of the light emitting diodes is greater than 7:4.

3. The therapy light of claim 2, wherein the ratio of the cumulative cross-sectional area of the airflow apertures to the cumulative cross-sectional area of the light emitting diodes is less than 10:4.

4. The therapy light of claim 1, wherein the diameter of the airflow apertures is between 0.5 millimeters and 1.5 millimeters.

5. The therapy light of claim 4, wherein the diameter of the airflow apertures is 1 millimeter.

6. The therapy light of claim 1, wherein the overall density of the airflow apertures in the ventilated area of the circuit board is fifteen airflow apertures per square centimeter.

7. The therapy light of claim 1, wherein said airflow apertures are arranged in a grid pattern.

8. A circuit board assembly comprising:

a circuit board having a front face and a back face;

a plurality of light emitting diodes operatively mounted on said front face of said circuit board;

a plurality of airflow apertures in said circuit board disposed adjacent said light emitting diodes such that said front face and said back face of said circuit board are in airflow communication one with the other, wherein the ratio of the cumulative cross-sectional area of the airflow apertures to the cumulative cross-sectional area of the light emitting diodes is greater than 3:2 and;

wherein the overall density of the airflow apertures in a ventilated area of the circuit board is between ten airflow apertures per square centimeter and twenty airflow apertures per square centimeter.

9. The circuit board assembly of claim 8, wherein the ratio of the cumulative cross-sectional area of the airflow apertures to the cumulative cross-sectional area of the light emitting diodes is greater than 7:4.

10. The circuit board assembly of claim 9, wherein the ratio of the cumulative cross-sectional area of the airflow apertures to the cumulative cross-sectional area of the light emitting diodes is less than 10:4.

11. The circuit board assembly of claim 8, wherein the diameter of the airflow apertures is between 0.5 millimeters and 1.5 millimeters.

12. The circuit board assembly of claim 11, wherein the diameter of the airflow apertures is 1 millimeter.

13. The therapy light of claim 8, wherein the overall density of the airflow apertures in the ventilated area of the circuit board is fifteen airflow apertures per square centimeter.

* * * * *